US00PP31760P2

(12) United States Plant Patent
Van Swieten

(10) Patent No.: US PP31,760 P2
(45) Date of Patent: May 12, 2020

(54) ***PHALAENOPSIS* ORCHID PLANT NAMED 'PHALGANZI'**

(50) Latin Name: ***Phalaenopsis* hybrid**
Varietal Denomination: PHALGANZI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,295

(22) Filed: Mar. 20, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database Nov. 19, 2019 [online] retrieved on Nov. 19, 2019, retrieved from the Internet at https://www3.wipo.int/pluto/user/en/index.jsp, one page. (Year: 2019).*
EU Community Plant Variety Rights Application No. 2018/1155, Application n°A201801069, filed Apr. 24, 2018, 8 pages.
EU Community Plant Variety Office Official Gazette, 3.2018, Jun. 15, 2018, cover page and pp. 35, 55.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALGANZI', particularly characterized by having very light purple, large flowers with reddish-purple shade and light purple lips, 1 to 2 peduncles that are long, leaves that are oblong, and is propagated by meristem tissue culture, is disclosed.

3 Drawing Sheets

Genus and species: *Phalaenopsis* hybrid.
Variety denomination: 'PHALGANZI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGANZI'.

The new *Phalaenopsis* plant is a product of a planned breeding program conducted by the inventor in Bleiswijk, The Netherlands. The objective of this breeding program was to create a new *Phalaenopsis* plant with numerous attractive very light purple, large flowers with reddish-purple shade and light purple lips, suitable for potted plant production.

The new *Phalaenopsis* plant 'PHALGANZI' is a result of cross-pollination made by the inventor in April 2008 in Bleiswijk, The Netherlands, of the proprietary female, or seed parent, *Phalaenopsis* hybrid '10597-01' (unpatented) with the proprietary male, or pollen parent, *Phalaenopsis* hybrid '28571-01' (unpatented).

The new *Phalaenopsis* was selected by the inventor as a single plant within the progeny of the stated cross-pollination in a controlled greenhouse in Bleiswijk, The Netherlands, in July 2011. Asexual reproduction of the new *Phalaenopsis* plant by meristem tissue culture since 2017 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2018, by Applicant who obtained the subject matter disclosed directly from the Inventor. 'PHALGANZI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGANZI' as a new and distinct variety of *Phalaenopsis* plant:

1) Very light purple, large flowers with reddish-purple shade and light purple lips;
2) 1 to 2 peduncles;
3) Peduncle is long; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, The Netherlands, from 50-week-old plants in February 2019. Colors in the photographs may differ from the color values cited in the detailed botanical description, which accurately describe the actual colors of the new variety.

DESCRIPTION OF THE NEW VARIETY

Figure 1:
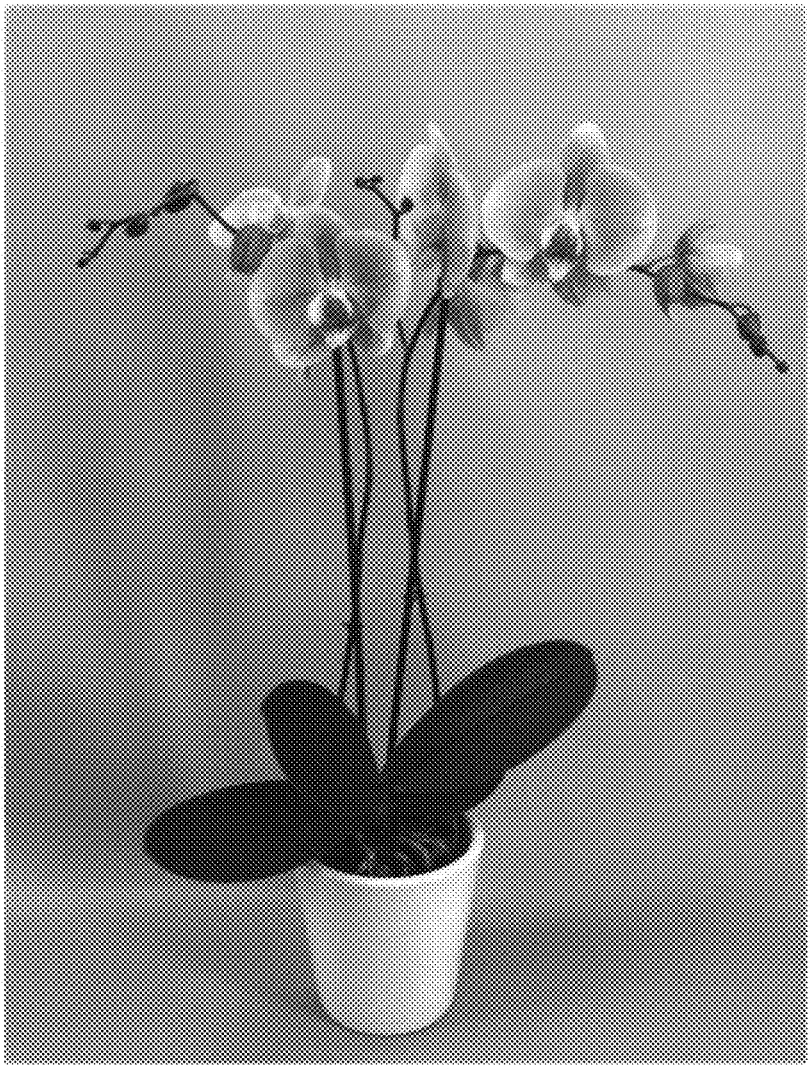
FIG. 1 shows the overall plant habit, including blooms, buds, and foliage of 'PHALGANZI'.
Figure 2:
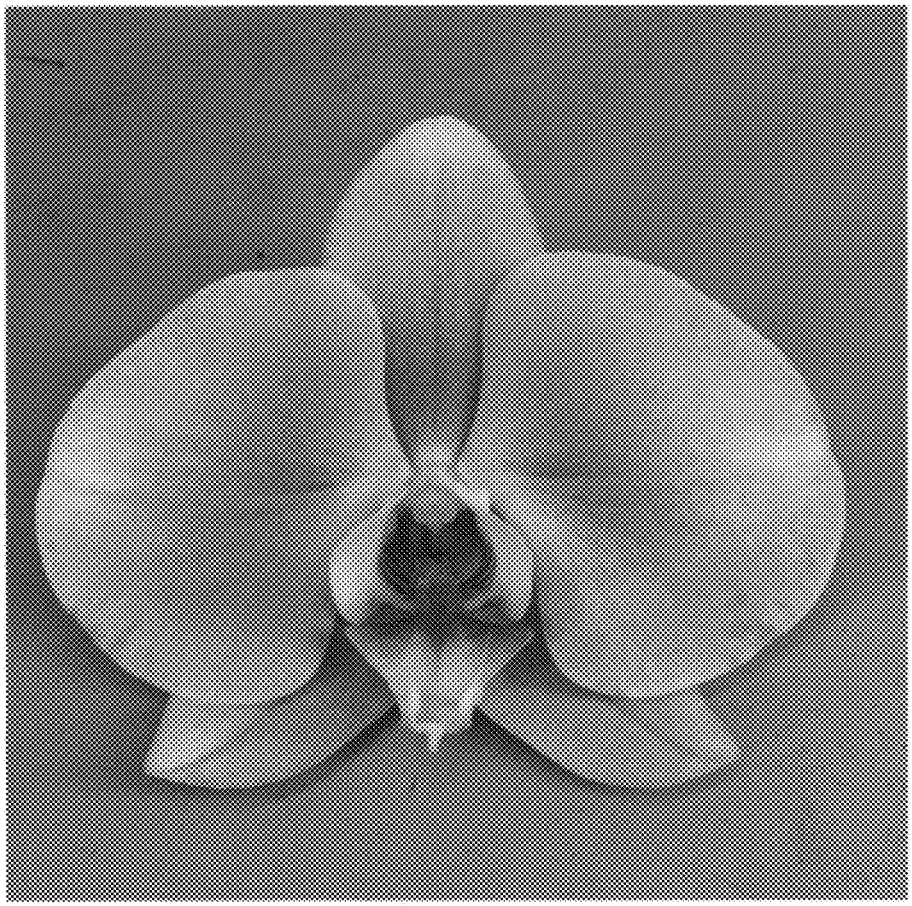
FIG. 2 shows a close-up of a flower of 'PHALGANZI'.
Figure 3:
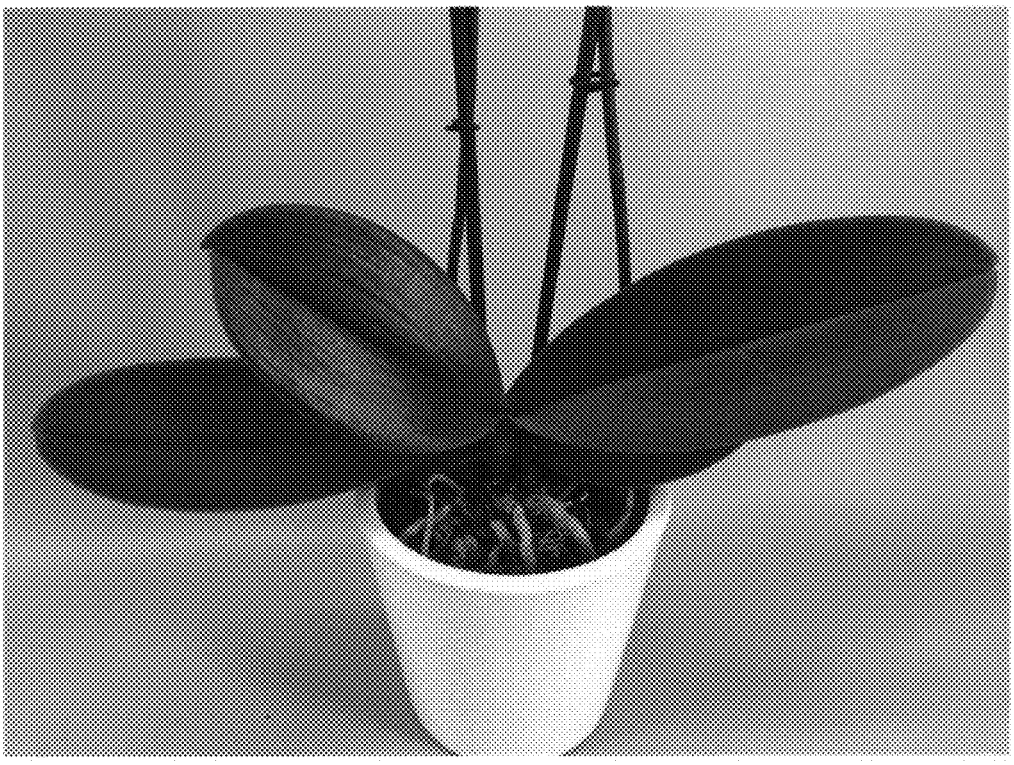
FIG. 3 shows an overhead view of the leaves of 'PHALGANZI'.

The following detailed description sets forth the distinctive characteristics of 'PHALGANZI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in February 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALGANZI'.

Parentage:

*Female parent.*—*Phalaenopsis* cultivar '10597-01' (unpatented).

*Male parent.*—*Phalaenopsis* cultivar '28571-01' (unpatented).

Propagation:

*Type.*—Meristem tissue culture.

Roots:

*Root description.*—Greyed-green (between RHS 190B and 190C) colored roots with branching lateral roots having yellow-green (RHS 144C) colored root tips.

Plant:

*Commercial crop time to flowering.*—Following asexual propagation (in-vitro), the rooted cuttings grow for 20-24 weeks. After transplantation into 12-cm pots, the plants are finished after 48 to 50 weeks.

*Growth habit of peduncle.*—Upright to slightly pendant with raceme to panicle inflorescence.

*Height (from soil level to top of inflorescence).*—Approximately 59.0 cm to 69.0 cm.

*Width (measured from leaf tips).*—About 34.0 cm to 39.0 cm.

*Vigor.*—Moderate.

Leaves:

*Mature leaves.*—Quantity per plant: 6 to 8 leaves are produced before flowering. Length (fully expanded): 17.0 cm to 20.0 cm. Width: 7.5 cm to 8.5 cm. Shape: Oblong. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 147A. Lower surface: RHS 147B. Texture (upper surface): Rough. Thickness: 2.6 mm to 3.1 mm. Venation: Pattern: Parallel. Color of the midvein: Upper surface: RHS 147A. Lower surface: RHS 147B.

Peduncle:

*Quantity per plant.*—1 to 2.

*Number of flowers per peduncle.*—8 to 12.

*Length.*—59.0 cm to 69.0 cm.

*Diameter.*—4.9 mm to 5.1 mm.

*Strength.*—Strong.

*Aspect.*—Upright to slightly pendant.

*Texture.*—Smooth.

*Color.*—Mix of green (RHS 146B) and brown (RHS 200C).

*Internode length.*—4.5 cm to 5.5 cm.

Inflorescence description:

*Appearance.*—Upright to slightly pendant, raceme to panicle inflorescence with bilaterally symmetrical flowers that open in succession beginning with the lowermost flower.

*Inflorescence size.*—Height (from base to tip): 320.0 mm to 370.0 mm. Diameter: 130.0 mm to 150.0 mm.

*Flowering time.*—First flowers can be expected 10 to 11 months after planting in a 12-cm pot.

*Flower.*—Height: 107.0 mm to 112.0 mm. Diameter: 120.0 mm to 125.0 mm. Depth of lip: 30.0 mm to 32.0 mm.

*Flower longevity.*—On the plant: 16 to 22 weeks.

*Fragrance.*—Absent.

*Flower bud.*—Average size: Large. Length: 27.0 mm to 29.0 mm. Width: 22.0 mm to 24.0 mm. Shape: Egg shaped. Color: Purplish-red (RHS N77B) with a touch of yellow-green (RHS 195B).

*Petals.*—Arrangement: Open/free. Shape: Semi-circular. Apex: Rounded to slightly emarginated asymmetric. Margin: Slightly wavy. Length (from base to tip): 55.0 mm to 57.0 mm. Width: 68.0 mm to 70.0 mm. Position of the broadest part of the petal: Toward the base. Color (when fully opened): Upper surface: Basic color: Very light purple (RHS 76C). Over color: White (RHS NN155C) at the base and apex and light reddish-purple shade (RHS N78D) near the base to the center. Lower surface: Basic color: Very light purple (RHS 76B). Over color: Light purple (RHS 76A) toward center. Number of spots, netting and stripes: None.

*Dorsal sepal.*—Shape: Elliptic. Apex: Obtuse symmetric. Margin: Entire. Length (from base to tip): 57.0 mm to 59.0 mm. Width: 36.0 mm to 38.0 mm. Color (when fully opened): Upper surface:. Basic color: Very light purple (RHS 76C). Over color: White (RHS NN155C) at the base and purplish-pink (RHS N78C) near the base to the center. Lower surface: Basic color: Light reddish-purple (RHS N78D). Over color: Slightly yellow-green (RHS 196B) in the middle; very light purple (RHS 76B) toward apex. Number of spots, netting and stripes: None.

*Lateral sepals.*—Shape: Ovate. Apex: Obtuse asymmetric. Margin: Slightly ruffled at the base. Length (from base to tip): 59.0 mm to 61.0 mm. Width: 33.0 mm to 35.0 mm. Color (when fully opened): Upper surface: Basic color: Very light purple (RHS 76B). Over color: Light yellow-green (RHS 145D) at the base; few, small spots (RHS 71A). Lower surface: Basic color: Light reddish-purple (RHS N78D). Over color: Light yellow-green (RHS 193A to 193B). Number of netting and stripes: None.

*Labellum* (*lip*).—Whiskers: Present. Length of whiskers: 25.0 mm to 27.0 mm. Color of whiskers: Slightly very light purple (RHS 76C) at the base and white (RHS NN155C) toward the tip.

*Lateral lobe.*—Shape: Type V (as described in the International Union for the Protection of New Varieties of Plants (UPOV) Test Guidelines for *Phalaenopsis*); spatulate. Margin: Wavy. Length: 25.0 mm to 27.0 mm. Width: 19.0 mm to 21.0 mm. Color: White (RHS NN155C); dark red stripes (RHS 187B and 187C) at the base; greenish-yellow (RHS 153C) and dark reddish-orange (RHS 178B) on sides toward base. Number of spots, netting and stripes: Few stripes.

*Apical lobe.*—Shape: Triangular. Margin: Entire. Length: 25.0 mm to 27.0 mm. Width: 28.0 mm to 30.0 mm. Color: Purplish-red (RHS 187D) at the base with dark greenish-yellow wings (RHS 152D); very light purple (RHS 76C) toward whiskers. Number of spots and stripes: None.

*Callus.*—Average size: Large. Height: 7.0 mm to 9.0 mm. Length: 6.0 mm to 7.0 mm. Width: 5.0 mm to 6.0 mm. Color: Yellow (RHS 14A); spotted (RHS 178A).

*Pubescence.*—Absent.

Reproductive organs:

*Column.*—Length: 10.0 mm to 12.0 mm. Diameter: 5.8 mm to 6.1 mm. Color: White (RHS NN155C) with light purple region (RHS 76A) in the middle.

*Pollinia.*—Quantity: 2. Diameter: 1.1 mm to 1.3 mm. Color: Orange (RHS 25A).

*Ovary.*—Length: 12.0 mm to 14.0 mm. Diameter: 2.6 mm to 2.9 mm. Color: Yellow-green (RHS 148D) and slightly very light purple (RHS 76B) toward the flower.

*Pedicel.*—Length: 43.0 mm to 45.0 mm. Diameter: 3.1 mm to 3.4 mm. Color: Green (between RHS 146A and 146B) at the base; yellow-green (RHS 148D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGANZI' differs from female parent plant '10597-01' (unpatented) in that 'PHALGANZI' has flowers with an upper surface basic color of very light purple and a shaded pattern, whereas '10597-01' has flowers with an upper surface basic color of white and an even pattern.

'PHALGANZI' differs from male parent plant '28571-01' (unpatented) in that 'PHALGANZI' has flowers with an upper surface basic color of very light purple (RHS 76C) and a shaded pattern, whereas '28571-01' has flowers with an upper surface basic color of light reddish-purple (RHS N78D) and a dotted pattern.

'PHALGANZI' is most similar to the commercial *Phalaenopsis* plants named 'PHALAGUC' (unpatented) and 'PHALMACHE' (unpatented). 'PHALGANZI' differs from the commercial variety 'PHALAGUC' in that 'PHALGANZI' has obtuse dorsal sepal apexes, lateral sepals with a spotted pattern, and whiskers that are slightly very light purple at the base and white toward the tip, whereas 'PHALAGUC' has emarginated dorsal sepal apexes, lateral sepals with a dotted pattern at the base, and whiskers that are very light purple with yellow tips. Additionally, 'PHALGANZI' has larger flowers, longer dorsal sepals, and longer whiskers than 'PHALAGUC'.

'PHALGANZI' differs from the commercial variety 'PHALMACHE' in that 'PHALGANZI' has lateral sepals with a spotted pattern, and whiskers that are slightly very light purple at the base and white toward the tip, whereas 'PHALMACHE' has lateral sepals with a striped pattern, and whiskers that are reddish-purple. Additionally, 'PHALGANZI' has larger flowers, longer dorsal sepals, and longer whiskers than 'PHALMACHE'.

I claim:

1. A new and distinct variety of *Phalaenopsis* plant named 'PHALGANZI', substantially as described and illustrated herein.

* * * * *